United States Patent
Schmid et al.

[11] Patent Number: 6,134,000
[45] Date of Patent: Oct. 17, 2000

[54] APPARATUS FOR SIMULTANEOUSLY MONITORING REACTIONS TAKING PLACE IN A PLURALITY OF REACTION VESSELS

[75] Inventors: Karl Schmid, Pfäffikon; Rolf Schneebeli, Mettmenstetten, both of Switzerland

[73] Assignee: Roche Diagnostics Corporation, Indianapolis, Ind.

[21] Appl. No.: 09/303,179

[22] Filed: Apr. 30, 1999

[30] Foreign Application Priority Data

May 1, 1998 [EP] European Pat. Off. .............. 98810394

[51] Int. Cl.⁷ ...................................... G01N 1/10
[52] U.S. Cl. .......................... 356/246; 356/440; 356/417; 385/12; 250/227.23
[58] Field of Search ..................... 356/244, 246, 356/432, 436, 440, 301; 385/12; 422/64, 104, 67, 99; 435/286.1, 303.1; 250/227.23, 227.18

[56] References Cited

U.S. PATENT DOCUMENTS

| | | |
|---|---|---|
| 3,992,631 | 11/1976 | Harte . |
| 4,647,210 | 3/1987 | Morris et al. ............................ 356/410 |
| 5,473,437 | 12/1995 | Blumenfeld . |
| 5,523,845 | 6/1996 | Honzawa et al. ....................... 356/440 |

FOREIGN PATENT DOCUMENTS

| | | |
|---|---|---|
| 0 580 362 | 1/1994 | European Pat. Off. . |
| 0 642 831 A1 | 8/1994 | European Pat. Off. . |
| 0 642 831 | 3/1995 | European Pat. Off. . |

OTHER PUBLICATIONS

The following references haVe been cited and commented in THE basic European patenT application 98810394.1 in order to illustrate prior art: International Application Publication #WO A 95/30139; Perkin–Elmer Corporation Apr. 19, 1995.

Patent Abstracts of Japan vol. 012, No. 350 & JP 63 103943 A; Oct. 20, 1988; May 9, 1988; Shimadzu Corp.

*Primary Examiner*—Hoa Q. Pham
*Attorney, Agent, or Firm*—Gibbons, Del Deo, Dolan, Griffinger, & Vecchione

[57] ABSTRACT

The apparatus comprises a square, metallic vessel holder with twenty-four chambers arranged to smoothly hold in an upright position changeable, transparent reaction vessels used to carry biological reaction liquids of about 100 μl. At the side walls of the chambers are arranged two connectors with associated boreholes. Within these holes are removably fixed first and second optic fibers. These fibers are connected in such a manner, that the axial extensions of the fibers meet one another approximately at a same point of the chamber's axis, and in such a manner, that light escaping from the first fibers cannot reach the second fibers directly. The open ends of the fibers are connected to a common light source and individually to associated light receivers, respectively.

14 Claims, 4 Drawing Sheets

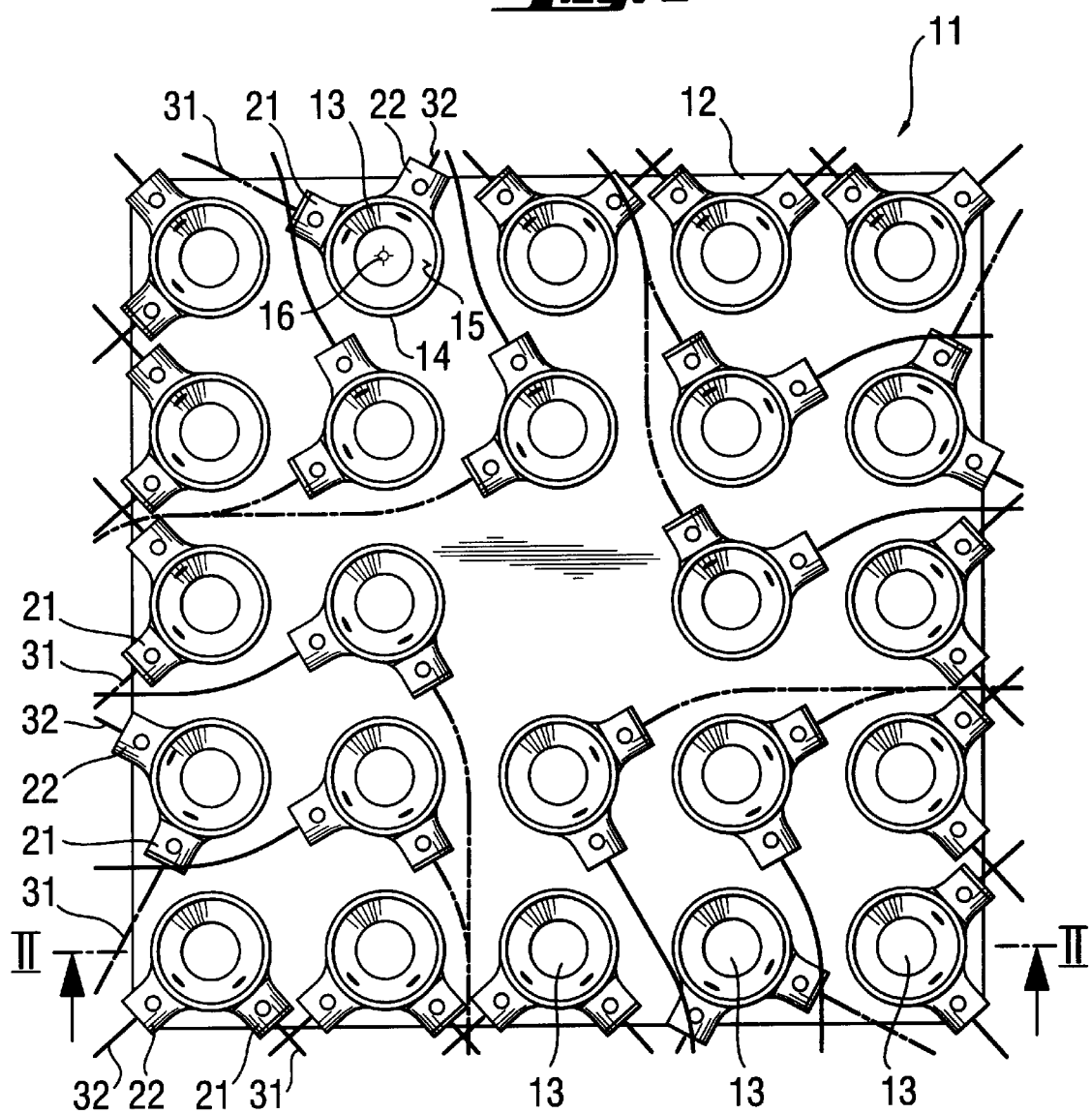

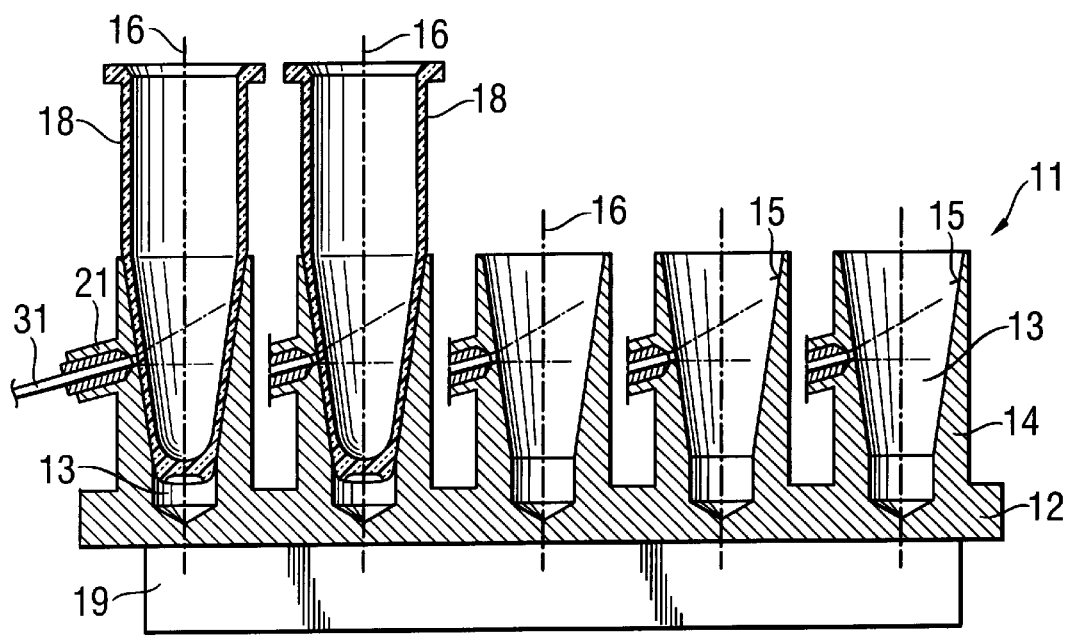

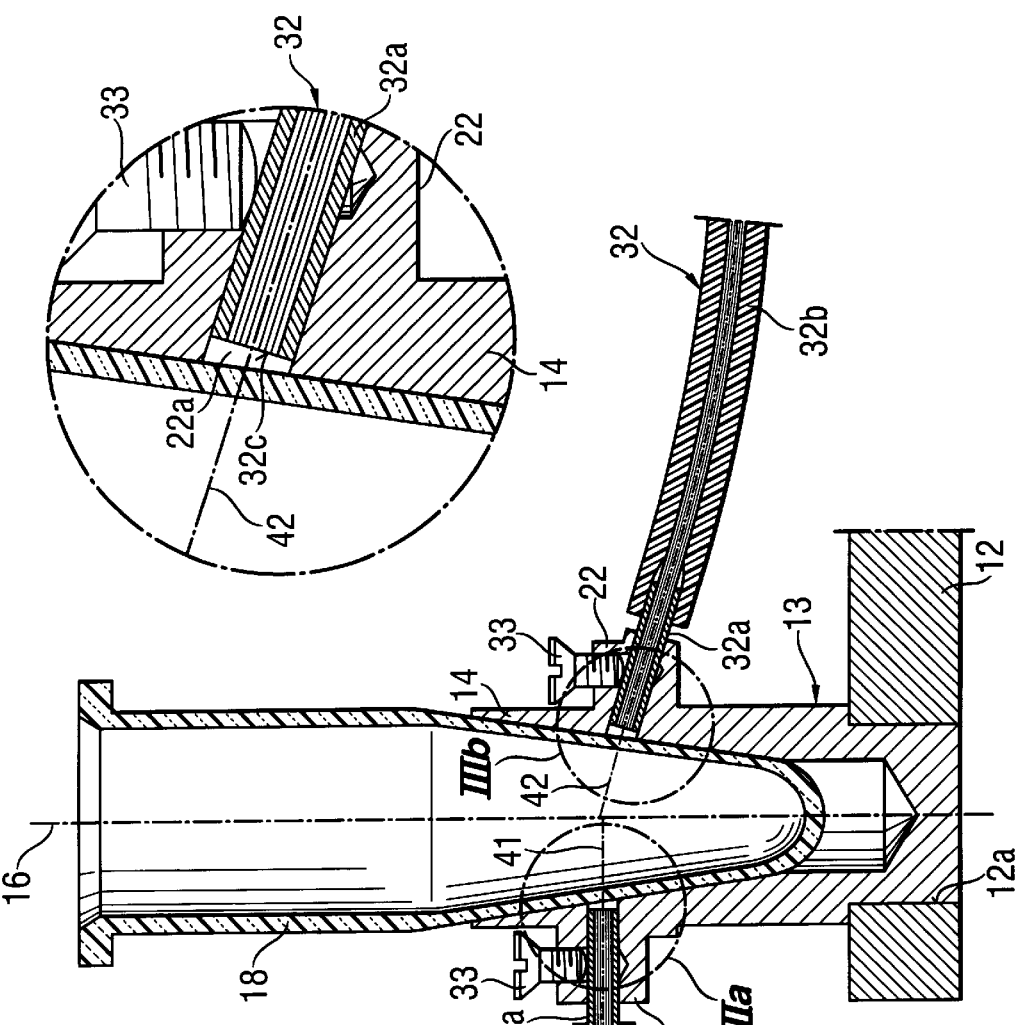

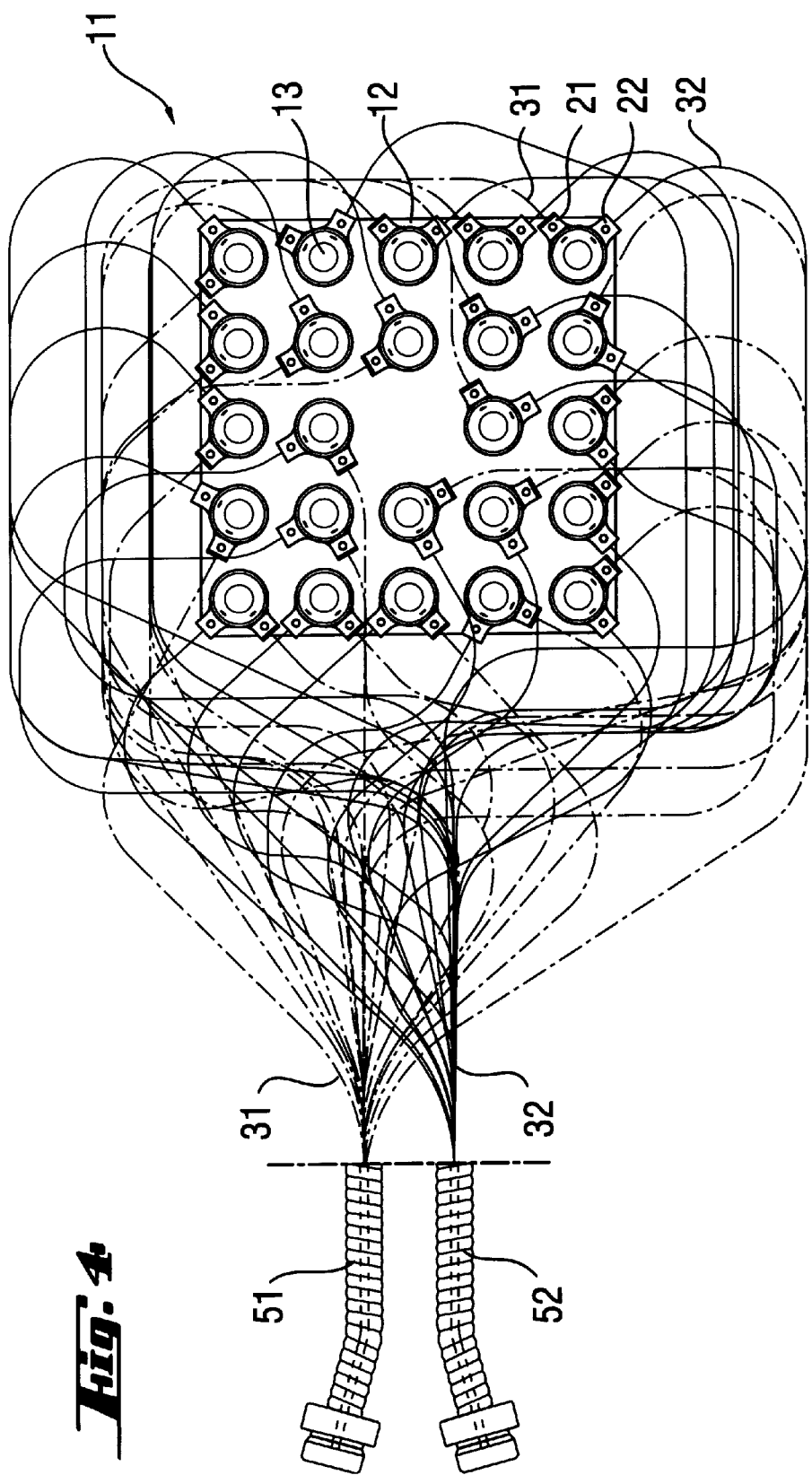

APPARATUS FOR SIMULTANEOUSLY MONITORING REACTIONS TAKING PLACE IN A PLURALITY OF REACTION VESSELS

RELATED APPLICATIONS

This application is related to the European Patent Application No. 98810394.1 filed on May 1, 1998.

BACKGROUND OF THE INVENTION

1. Field of the Invention

The present invention concerns an apparatus for simultaneously monitoring reactions taking place in a plurality of reaction vessels comprising a metallic vessel holder with a plurality of chambers, the side wall of each of these chambers being formed to smoothly hold in an upright position a removable and transparent reaction vessel.

More particularly, the invention concerns an apparatus wherein the monitoring is carried out by measuring fluorescence light emitted by sample-reagent mixtures when they are excited by light provided by a suitable light source, such as a light of short wave-length.

2. Description of the Prior Art

An apparatus for the automatic execution of temperature cycles is known from EP 0 642 831 A1. This apparatus comprises a circular holder for twelve reaction vessels, each of these vessels containing sample-reagent liquid mixtures of about 100 µl. The holder is metallic and allows fast transmission of the different temperatures of the cycles from a controlled Peltier element to the mixtures.

A system for real time detection of nucleic acid amplification products is known from WO 95/30139 A1. This system allows fluorescence-based measurements on a plurality of sample-reagent liquid mixtures within small vessels at different, varying temperatures. The excitation light arrives at the vessels from the top side via a fiber optic and a focal lens. The fluorescent light is collected via the same way in opposite direction and is transmitted to a centralized optical separation and analyses component.

There are important disadvantages of the described devices. With the circular array of vessels disclosed by EP 0 642 831 A1 only a relatively low number of vessels can be positioned on a single Peltier element. Therefore, only a small part of the area available on a Peltier element for thermal cycling of such vessels is used.

In order to carry out temperature cycles on a high number of reaction vessels arranged in a circle, it would be necessary to use more than one Peltier element for cooling and heating. This is not desirable because Peltier elements are rather expensive. In the apparatus disclosed by WO 95/30139, the excitation light path and the fluorescence light path are close to each other, and this increases the possibility of undesirable interferences.

Therefore, with the structure of the above-mentioned known devices it is not possible to provide a very compact array of reaction vessels which is suitable for performing thermal cycling of a plurality of sample-reagent mixtures contained in reaction vessels positioned on a thermal block.

SUMMARY OF THE INVENTION

It is the object of the present invention to provide an apparatus which comprises a very compact array of reaction vessels, which is suitable for performing an efficient thermal cycling of the sample-reagent mixtures contained in a plurality of reaction vessels, and which allows optical real time measurements. More particularly, the present invention provides an apparatus in which thermal cycling of a larger number of reaction vessels using a single Peltier element can be accomplished.

According to the present invention this objective is attained with an apparatus which comprises a plurality of first optic fiber light guides, each of which connects the inside of the side wall of one of said chambers with a light source, and a plurality of second optic fiber light guides, each of which connects the inside of the side wall of one of said chambers with a light receiver, wherein in each of said chambers the axial extensions of optic fiber light guides connected to the chamber meet one another approximately at a same point of the longitudinal axis of the chamber, and in such a manner, that light escaping from one of the light guides is not able to reach the other light guide connected to the chamber.

A main advantage of the present invention is that it comprises a very compact array of reaction vessels and is therefore suitable for performing efficient thermal cycling of the sample-reagent mixtures contained in the reaction vessels. A further advantage of the present invention is that in spite of the short distance between neighboring reaction vessels and of short distance between excitation light and fluorescence light fibers optically connected to each reaction vessel, a stray light emanating from an excitation beam directed to a sample-reagent mixture in a reaction vessel cannot interfere with measurement of fluorescence light emitted from the sample-reagent mixture. The apparatus according to the present invention is therefore in particularly suitable for monitoring simultaneously reactions taking place in a plurality of reaction vessels by means of fluorescence measurements which are carried out at any time, especially during thermal cycling of sample-reagent mixtures contained in the reaction vessels.

For a better understanding of the present invention, preferred embodiments thereof are described in more detail hereinafter with reference to the accompanying drawings.

BRIEF DESCRIPTION OF THE DRAWINGS

FIG. 1 is a top view of a vessel holder.

FIG. 2 is a vertical cross-section through the vessel holder shown in FIG. 1.

FIG. 3 is an enlarged representation of a vertical cross-section through one of the chambers of the vessel holder and through two planes which form an angle of 90 degrees and pass through the centers of connectors like those shown in FIG. 1.

FIGS. 3a and 3b show enlarged representations of the areas IIIa respectively IIIb in FIG. 3.

FIG. 4 is a second top view of the vessel holder.

DETAILED DESCRIPTION OF THE INVENTION

The present invention is an apparatus for monitoring reactions at any time, simultaneously and using light. As shown in FIG. 1, the invention comprises a metallic vessel holder 11 with a plurality of chambers 13, having side walls 14 formed to smoothly hold in an upright position independent, changeable, transparent and conical reaction vessels 18, inside which vessels 18 the reactions take place. There are first optic fibers 32 connecting the insides of the side walls 14 of all the chambers 13 with a light source, and second optic fibers 31 connecting the insides of the side walls 14 of all of the chambers 13 with at least one light receiver, wherein the first 32 and second fibers 31 connecting the insides in such a manner, that the axial extensions 41 and 42 of the fibers 31 and 32 meet one another approximately at a same point of the longitudinal axis 16 of the chambers 13 and in such a manner that light escaping from the first fibers 32 is not able to directly reach the second fibers 31.

FIG. 1 shows a top view on a vessel holder 11, FIG. 2 a vertical cross-section through the vessel holder, both Figures being enlarged by a factor of about 2 with respect to the real size of the objects shown.

In the embodiment of the invention shown in FIGS. 1 and 2, the holder 11 comprises a quadratic ground plate 12 the bottom side of which lies on a plane. The upper part of plate 12 contains a matrix-like array of twenty-four chambers 13.

Each of these chambers has upright side walls 14 and a circular cross-section in a plane perpendicular to its longitudinal axis. The outer side of side walls 14 is of cylindrical shape; the inner side 15 of side walls 14 defines a chamber the cross-section of which diminishes towards the bottom of the chamber. Each of the chambers 13 receives the lower part of a commercially available, removable reaction vessel 18 suitable for receiving about 100 µl of liquid. The lower part of the reaction vessel has a shape which smoothly fits into the inner side of a chamber 13 when the vessel is positioned in the latter chamber.

The flat bottom side of the ground plate 12 is arranged on a single Peltier element 19 used for heating and cooling of the vessel holder 11 and the reaction vessels 18 inserted in the chambers 13 of ground plate 12. For good thermal conduction, the vessel holder 11 is metallic, and it is preferably made of aluminum. In the following description, the term optic fiber is used to designate an optic fiber light guide which is not necessarily a single fiber, but which is preferably a bundle of thin optic fibers, e.g. a bundle of about 50 to 100 optic fibers, such a bundle having a diameter of about 0.5 mm.

At each chamber wall 14 are arranged two connectors 21 and 22. These connectors are used to fix optic fibers 31 and 32 and are arranged under an angle of about 90 degrees when seen in top view.

FIG. 3 shows an enlarged representation, by a factor of about 5:1, of a vertical cross-section of chamber 13 and of optic fiber light guides connected thereto. This is a cross-section along two different planes passing along the longitudinal axis 16 of chamber 13. One of these planes passes through the axis of a connector similar to connector 21 in FIG. 1 and the other plane passes through the axis of a connector similar to connector 22 in FIG. 1.

As shown by FIG. 3, the ground plate 12 has boreholes 12a, into which the circular chamber 13 is inserted and fixed, e.g. by pressing or soldering, the base plane afterwards being polished. When a reaction vessel 18 is inserted in a chamber 13, the lower part of vessel 18 smoothly fits into the inner side of the side walls 14 of the chamber 13. As shown by FIG. 3a, the side wall 14 has a first connector 21 which has a horizontal borehole 21a.

An end part of an optic fiber 31, which comprises a bundle of optic fibers having a bundle diameter of about 0.5 mm and which is sheathed by a flexible cover 31b with an outer diameter of about 1.5 mm is inserted into the borehole 21a of the connector 21. The end part of optic fiber 31 which is inserted into borehole 21a is surrounded by a rigid guiding tube 31a. One end of this tube is shoved under the flexible cover 31b and its other end is fixed by a screw 33 in such a way, that the open end of the fiber 31 is close to, but is spaced from the wall of the reaction vessel 18. The front end 31c of fiber 31 is a polished surface which lies in a plane which is parallel to the longitudinal axis 16 of the chamber 13. The axial extension 41 of the fiber 31 meets the longitudinal axis 16 of the chamber 13 or the vessel 18, respectively. The space between the front end 31c and the wall of the vessel 18 is established the by help of a ball gauge.

As shown in FIG. 3, the connector 22 is arranged at the side wall 14 a bit lower than connector 21. The connector bore hole 21a of the connector 22 is inclined with respect to the longitudinal axis 16 of the chamber and the axial extension 42 of bore hole 22a meets the longitudinal axis 16 of the chamber 13 nearly at the same point as the extension 41 of bore hole 21a.

An end part of an optic fiber 32, which comprises a bundle of optic fibers having a bundle diameter of about 0.5 mm and which is sheathed by a flexible cover 32b with an outer diameter of about 1.5 mm is inserted into borehole 22a of the connector 22. The end part of optic fiber 32 which is inserted into the borehole 22a is surrounded by a rigid guiding tube 32a. One end of this tube is shoved under the flexible cover 32b and its other end is fixed by a screw 33 in such a way, that the open end of the fiber 32 is close to, but is spaced from the wall of the reaction vessel 18. The front end 32c of the fiber 32 is a polished surface which lies in a plane which is inclined with respect to the longitudinal axis 16 of the chamber 13. The axial extension 42 of the fiber 32 meets the longitudinal axis 16 of the chamber 13 or the vessel 18, respectively. The space between the front end 32c and the wall of the vessel 18 is established by help of a ball gauge.

As shown by FIG. 3, the axial extensions 41 and 42 do not meet exactly at the same point of the axis 16. But when there is a reaction liquid within the vessel 18, refraction of the light beams transmitted by optical fibers 31 and 32 will cause these beams to meet at a point.

Further, the construction of the present invention is such that the angle between axial extension 41 and the portion of the side wall of the vessel 18 which is adjacent to the connector 21 is equal to the angle between axial extension 42 and the portion of the side wall of the vessel 18 which is adjacent to the connector 22. Therefore, the light beams transmitted by optical fibers 31 and 32 find the same geometric conditions.

To prevent undesirable light reflections, the entire holder 11 including the chambers 13 are colored black such as by anoxic coating.

As shown by FIG. 4, all optic fibers 31 are bundled and held together such as by a helical tape to form a bundle 51, and all optic fibers 32 are also bundled and held together such as by a helical tape to form a bundle 52. Bundles 51 and 52 extend in the same direction. It is important that all of the fibers 31 and 32 have about the same length and that none of the fibers 31 or 32 is bent sharply. The minimum radius of curvature of fibers like 31 and 32, which are each a bundle of thin optic fibers, is much smaller than the radius of curvature of a single optic fiber having the same total cross-section. By using optic fiber bundles 31 and 32, it is thus possible to make bows having a small radius of curvature and therefore to accommodate many fibers in a relatively small space.

As shown by FIGS. 1 and 4, each fiber 31 and 32 passes at most two chambers 13 on its way from its connectors 21 and 22 respectively, to the space outside the area where the vessel holder 11 is located (FIG. 1). This is made possible on the one hand by the arrangement of the chambers 13 and their connectors 21 and 22 and the above described construction of connectors 21 and 22 and their associated boreholes 21a and 22a (see FIGS. 3a, 3b) which lead fibers 31 and 32 into two different planes between the chambers 13. These arrangements allow crossing of fibers 31 with fibers 32 and vice versa.

As a whole, the structure comprising a vessel holder 11 with a side length of about 4 cm and with a distance of 9 mm between longitudinal axis 16 of adjacent chambers 13 is very compact. A measure of the compactness of this structure is the ratio of the cross-section surface of all the reaction vessels 18 as shown by the top view according to FIG. 1 to the surface available on the vessel holder 11 for positioning the vessels 18. This ratio is larger than 0.6 mm. The structure just mentioned guarantees uniform equal temperature all over the holder 11. For thermal cycling this temperature is modified by electrical control of Peltier element 19.

The vessel holder 11 is used within an apparatus for monitoring reactions of the liquid biological probes. These liquid probes with a volume of about 100 $\mu$l are filled into the reaction vessels 18 fixed in the chambers 13. This is done automatically with the help of a pipetting means. The reactions take place within the reaction vessels 18 and require cyclical temperature changes. At any time, the optic fibers 32 allow transmission of the excited light of a common light source, such as a halogen lamp with interference filter to get monochromatic light, to each of the chambers 13. This light escapes the front ends 32c of the fibers 32, passes through the transparent walls of the vessels 18 and reaches the liquid sample-reagent mixture, where the light beam undergoes refraction. The sample-reagent mixture contains fluorophores which upon excitation emit more or less fluorescence light as a result of the reaction. The fluorescence light is collected by the second optic fibers 31 and transmitted to 22a individual light receivers (not shown) such as photo diodes. The receiving signals of the light receivers are then measured for the individual reactions to be monitored.

It is important, that the ends of both fibers 31 and 32 are not optically connected with each other. With the above described configuration, fibers 31 only collect fluorescence light to be monitored. Stray light reflected at the wall of the reaction vessels 18, at the upper meniscus surface, or at particles inside the liquid probes does not reach the light receiver and has therefore no influence on the output signals thereof. The given geometry of the upright standing vessels 18, the conical wall of the vessels 18 and the horizontal direction of the axial extensions 41 and 42 result in a minimum of stray light. Foam at the surface of the liquid probes or condensations inside the vessel 18 have no influence. Daylight may be minimized by daylight filters or preferably by surrounding the vessel holder 11 by a light tight box.

In accordance with one aspect of the present invention, there may be a plurality of more or less than 22a chambers 13 at the vessel holder 11.

In accordance with another aspect of the present invention, the vessel holder 11 can be formed as a square, a rectangle, a circle, etc. The chambers 13 may be arranged in a matrix-like configuration with lines and columns that are rectangular or staggered.

In accordance with yet another aspect of the present invention, the angle between both fiber connectors 21 and 22 can be 90 degrees as shown, but may be larger or less. Generally, the angle must be small enough so that no light escaping the optic fiber 32 will be able to directly reach the other fiber 31 receiving light from the liquid probe.

In accordance with further aspect of the present invention, the boreholes 21a and 22a of the connectors 21 and 22 may not be horizontally oriented, e.g. the first leading upwards and the second leading downwards such that the axial extensions 41 and 42 meet at a same point of the longitudinal axis 16 of the chamber 13 or nearby.

In accordance with another aspect of the present invention, the optic fibers 31 and 32 may be fixed inside the boreholes 21a and 22a by means other than by the screws 33 shown in FIG. 3 such as by gluing. However, the screws 33 have an advantage because the fibers are easily exchangeable.

In another embodiment of the invention, the dimensions of the chambers 13 and the reaction vessels 18 may be variable. Furthermore, two or more different sizes may be used with the same vessel holder 11.

It should be understood, however, that the present invention herein illustrated and described is intended to be representative only, as many changes may be made therein without departing with the clear teachings of the invention. Accordingly, reference should be made to the following claims in determining the full scope of the invention, as it will be appreciated that the invention is susceptible to modification, variation and change without departing from the proper scope and fair meaning of the subjoined claims.

What is claimed is:

1. An apparatus for simultaneously monitoring reactions taking place in a plurality of reaction vessels, said apparatus comprising:

a metallic vessel holder having a plurality of chambers with the side wall of each of said chambers being formed to hold in an upright position a removable and transparent reaction vessel, wherein said side wall of each of said chambers comprises two connectors with associated boreholes, said connectors having axes which, when seen from a top view of said chamber, form an angle, the longitudinal axis of one of said boreholes being perpendicular to the longitudinal axis of said chamber and the longitudinal axis of the other of said boreholes being inclined with respect to the longitudinal axis of said chamber, the axial extensions of said boreholes meeting one another approximately at the same point of the longitudinal axis of said chamber;

a plurality of first optic fiber light guides, wherein each of said optic fiber light guides connects the inside of the side wall of one of said chambers with a light source;

a plurality of second optic fiber light guides, wherein each of said optic fiber light guides connects the inside of the side wall of one of said chambers with a light receiver; and said boreholes bearing the endpieces of said second and said first optic fiber light guides connect to said chambers, respectively.

2. An apparatus according to claim 1, wherein each of said plurality of first optic fiber light guides and each of said plurality of second optic fiber light guides are each a bundle of about 50 to 100 parallel fibers with each bundle having a diameter of about 0.5 mm.

3. An apparatus according to claim 2, wherein said plurality of said first optic fiber light guides and said plurality of said second optic-fibers are combined to form two independent bundles so that none of said optic fiber light guides passes at the side of more than two of said chambers and that between said chambers a segment of a first optic fiber light guide is arranged in a first plane and a segment of a second optic fiber light guide is arranged in a second plane which lies above said first plane.

4. An apparatus according to claim 1, wherein said vessel holder comprises a square ground plate carrying twenty-four chambers arranged in a matrix-like array.

5. An apparatus according to claim 4, wherein said ground plate is of aluminum having a plane bottom side being in contact with a single Peltier element.

6. An apparatus according to claim 4, wherein the distance between the longitudinal axis of the neighboring chambers is about 9 mm.

7. An apparatus according to claim 4, wherein the ratio of the cross-section surface of said chambers to the surface available for positioning said reaction vessels is larger than 0.6 mm.

8. An apparatus according to claim 4, wherein said plurality of said first optic fiber light guides and said plurality of said second optic fibers are combined to form two independent bundles so that none of said optic fiber light-guides passes at the side of more than two of said chambers and that between said chambers a segment of a first optic fiber light guide is arranged in a first plane and a segment of a second optic fiber light guide is arranged in a second plane which lies above said first plane.

9. An apparatus according to claim 1, wherein said endpieces are removably positioned within said boreholes and held therein by means of screws.

10. An apparatus according to claim 1, wherein said endpieces are fixed within said boreholes so that the front ends of the optic fibers are close to but spaced from the side wall of the reaction vessel inserted into said chamber.

11. An apparatus according to claim 1, wherein said plurality of said first optic fiber light guides and said plurality of said second optic fibers are combined to form two independent bundles so that none of said optic fiber light guides passes at the side of more than two of said chambers and that between said chambers a segment of a first optic fiber light guide is arranged in a first plane and a segment of a second optic fiber light guide is arranged in a second plane which lies above said first plane.

12. An apparatus according to claim 11, wherein said bundle of said plurality of first optic fiber light guides is connected to a single light source and each of said plurality of second optic fiber light guides which form the second bundle optic fiber light guides are connected individually to a light receiver.

13. An apparatus according to claim 1 wherein said axes of said connectors form an angle of about 90°.

14. An apparatus for simultaneously monitoring reactions taking place in a plurality of reaction vessels, said apparatus comprising:

a metallic vessel holder having a plurality of chambers with the side wall of each of said chambers being formed to hold in an upright position a removable and transparent reaction vessel;

a plurality of first optic fiber light guides, each of which ate a bundle of about 50 to 100 parallel fibers with each bundle having a diameter of about 0.5 mm, and each of said first fiber light guides connects the inside of the side wall of one of said chambers with a light source;

a plurality of second optic fiber light guides, each of which are a bundle of about 50 to 100 parallel fibers with each bundle having a diameter of about 0.5 mm, and each of said second optic fiber light guides connects the inside of the side wall of one of said chambers with a light receiver;

wherein in each of said chambers the axial extensions of optic fiber light guides connected to the chamber meet one another approximately at a same point of the longitudinal axis of said chamber and such that light escaping from one of said light guides is not able to reach the other light guide connected to said chamber; and wherein said side wall of each of said chambers comprises two connectors with associated boreholes, said connectors having axes which, when seen from a top view of said chamber, form an angle of about 90 degrees, the longitudinal axis of one of said boreholes being perpendicular to the longitudinal axis of said chamber and the longitudinal axis of the other of said boreholes being inclined with respect to the longitudinal axis of said chamber, the axial extensions of said boreholes meeting one another approximately at a point of the longitudinal axis of said chamber and said boreholes bearing the endpieces of said second and said first optic fiber light guide connected to the chamber, respectively.

* * * * *